US005118617A

United States Patent [19]

Ortega et al.

[11] Patent Number: 5,118,617

[45] Date of Patent: Jun. 2, 1992

[54] SAF POLYPEPTIDE, GENE CODING THEREFOR, SAF PROMOTER AND EXPRESSION METHODS FOR EXPRESSING FOREIGN DNA SEQUENCES IN STREPTOMYCES

[75] Inventors: Antonio D. Ortega, Benacazon; Jose A. Gil, Leon; Tomas V. Garcia, Leon; Juan F. Martin, Leon, all of Spain

[73] Assignee: Applied Research Systems ARS Holding N.V., Curacao, Netherlands Antilles

[21] Appl. No.: 410,706

[22] Filed: Sep. 22, 1989

Related U.S. Application Data

[63] Continuation-in-part of Ser. No. 354,265, May 19, 1989.

[51] Int. Cl.[5] .................... C12N 1/21; C12N 15/31; C12N 15/63; C12N 15/76

[52] U.S. Cl. .................... 435/69.1; 435/6; 435/71.2; 435/91; 435/169; 435/172.1; 435/172.3; 435/252.3; 435/252.35; 435/320.1; 435/886; 536/27; 530/350; 935/6; 935/8; 935/9; 935/22; 935/29; 935/33; 935/38; 935/39; 935/41; 935/59; 935/60; 935/61; 935/66; 935/72; 935/75

[58] Field of Search .............. 536/27; 530/350; 435/6, 435/69.1, 71.2, 91, 169, 172.1, 172.3, 252.3, 252.35, 320.1, 886; 935/6, 9, 22, 29, 59, 60, 61, 66, 72, 75

[56] References Cited

U.S. PATENT DOCUMENTS 4,745,056 5/1988 Guterman et al. .................... 435/68

OTHER PUBLICATIONS

Horinouchi et al., 1983, J. Bacteriol., vol. 155: 1238-1248.

*Primary Examiner*—Richard C. Peet
*Attorney, Agent, or Firm*—Browdy and Neimark

[57] ABSTRACT

The cloning and characterization of a newly isolated gene, referred to as saf (secondary metabolism activation factor) is disclosed. This gene encodes a new amino acid polypeptide, referred to as the SAF polypeptide, which directly or indirectly modulates the expression of extracellular enzymes in Streptomyces. DNA units or fragments which encode the SAF polypeptides are also disclosed, as are vectors containing said DNA, host organisms transformed with such vectors, and processes for preparing extracellular enzymes or heterologous polypeptides by culturing such host organisms.

30 Claims, 22 Drawing Sheets

PLASMIDS INSERTS IN pIJ702 pULAD1: BglII SstI SalGI KpnI SstI KpnI SalGI BamHI SalGI KpnI SstI BglII pULAD2: BglII/Sau3AI SalGI KpnI SstI KpnI SalGI BamHI SalGI BglII/Sau3AI pULAD16: BglII/Sau3AI KpnI SstI KpnI SalGI BamHI SalGI BglII pULAD18: BglII/Sau3AI SalGI KpnI SstI KpnI SalGI BglII/Sau3AI pULAD3: BglII SstI KpnI SalGI BglII

1 Kb 1 2 3 4 5 6 7

1 2 3 4 5 6 7

PLASMID
INSERT IN pIJ702
EXTRACELLULAR ENZYME PRODUCTION
Bgl II
Sst I
ORF1
Kpn I
Sal GI
Bgl II
mel
pULAD3 ++++
pULAD4 ++++
pULAD5 ++++
pULAD6 ++++
pULAD7 -
pULAD8 -
pULAD9 -
pULAD10 ++
pULAD11 -
pULAD12 -
pULAD13 -
pULAD14 ++

FIG.6A

```
BglII
AGATCTCCTCGTCCCACCGGCTGTCGAAGCTCCGCGCCTACAGCGCCATCGACTTCGAC   59

CGGGCGAAGTAGGAAGCGGCCGGCGACAAAACGGGGAGGGGCGGAAACGGTGGTCCGT   118

TTCCCGCCCCTGCCCGTAGGCCGTGCGCGTCCCGCCGGTGCGCGGCGTTCAGCCCGCCG   177

                                                       Sst
CCGCT          ATG TGC TCG GCC GTC GTC GCG GCG GCC GTG AGC   215
               Met Cys Ser Ala Val Val Ala Ala Ala Val Ser

I
TCG ATG TCC CGC CGT CGC CGC CGG GCC AGC GCC ACC CGG CGC TCC   260
Ser Met Ser Arg Arg Arg Arg Arg Ala Ser Ala Thr Arg Arg Ser

GCT GCG GTG AGC CCG CCC CAC ACT CCG TAC GGC TCG GGC TGC ATC   305
Ala Ala Val Ser Pro Pro His Thr Pro Tyr Gly Ser Gly Cys Ile
```

FIG.6B

```
AGC GCG TGC TCC TGG CAC TCC ACC ATC ACC GGA CAC CGG GCA CAG  350
Ser Ala Cys Ser Trp His Ser Thr Ile Thr Gly His Arg Ala Gln

ACC CGC TTG GCC GCC TCC TCG CGG GCC AGC CGG GCG GCG GTC GGC  395
Thr Arg Leu Ala Ala Ser Ser Arg Ala Ser Arg Ala Ala Val Gly

TCC TTC GAC GGG GCG AAG AAC AGG CCG GCC TCG TCG CGG CGG CAG  440
Ser Phe Asp Gly Ala Lys Asn Arg Pro Ala Ser Ser Arg Arg Gln

GCC GCA TCG GAA TGC CAG GGG CCC GCG TCG TCC TCC CGT GCG GGG  485
Ala Ala Ser Glu Cys Gln Gly Pro Ala Ser Ser Ser Arg Ala Gly

GTC CGC TGG GCC GGA ACG GCG GCG AAC GGC AGA GGC TGA          524
Val Arg Trp Ala Gly Thr Ala Ala Asn Gly Arg Gly ter

TGCGGCGGTTGCAGCACGGTCTACTCCTGACGACGGCTACGGCTTCGCGAGGATGAGTC  583
```

FIG.6C

```
GATGCAGCTCTCCCTACCCGCTGTGCGTACGCCTAAGCACGGAGCGCCACCAGCGCGCG  642

  KpnI
GGGTACCGGAATGCGCCCCCGCGGCCTTTTGGCCGATTACCGGAGGTCGCGCGCCCCGC  701

CGTATACCGTGCGCACCACCGTATTCAGTGGCCGAGGTGTTTGCGCAGCCGCTGCTGGA  760

GGTCCGCCACGAACTTGCCCCGCTTCGGCCTGGCTTCCACGCTGCCGAACACGGAATAG  819

CCGTTGACCACGACGACCGGTGCTTCCGGGTCCGCCGATTCGAGCGTCCGCACGTCGAA  878

                                                          S
GGTGCCGAAGACGCCCGTGCCGCTGCCGCGCAGGGAAATGTTCTCCGGCACCCGGACGT  937
stI
CGACGCTGCCGAAGATGGACGTCGCATTGATAACGGTGAGGCGTTGCCCGAAAAGCGCT  996
     BglII
TCGGTGAGATCT                                               1008
```

| | | | | | | | | | | | | | | | | | | |
|---|---|---|---|---|---|---|---|---|---|---|---|---|---|---|---|---|---|---|
| λCI | Gln | Glu | Ser | Val | Ala | Asp | Lys | Met | Gly | Met | Gly | Gln | Ser | Gly | Val | Gly | Ala | Leu |
| λCro | Gln | Thr | Lys | Thr | Ala | Lys | Asp | Leu | Gly | Val | Tyr | Gln | Ser | Ala | Ile | Asn | Lys | Ala |
| LacI | Leu | Tyr | Asp | Val | Ala | Glu | Tyr | Ala | Gly | Val | Ser | Tyr | Gln | Thr | Val | Ser | Arg | Val |
| Lex | Ala | Ala | Glu | Ile | Ala | Gln | Arg | Leu | Gly | Phe | Arg | Ser | Pro | Asn | Ala | Ala | Glu | Glu |
| Lex R | Arg | Ala | Glu | Ile | Ala | Gln | Arg | Leu | Gly | Phe | Arg | Ser | Pro | Asn | Ala | Ala | Glu | Glu |
| P22Rep | Gln | Ala | Ala | Leu | Gly | Lys | Met | Val | Gly | Val | Ser | Asn | Val | Ala | Ile | Ser | Gln | Trp |
| CAP | Arg | Gln | Glu | Ile | Gly | Asn | Ile | Val | Gly | Cys | Ser | Arg | Glu | Thr | Val | Gly | Arg | Ile |
| Fnr | Arg | Gly | Asp | Ile | Gly | Asn | Tyr | Leu | Gly | Leu | Thr | Val | Glu | Thr | Ile | Ser | Arg | Leu |
| Saf | Arg | Ala | Ala | Val | Gly | Ser | Phe | Asp | Gly | Ala | Lys | Asn | Arg | Pro | Ala | Ser | Ser | Arg |
| $AfsB_a$ | Gln | Arg | Arg | Tyr | Ala | Glu | Gly | Lys | Gly | Leu | Phe | His | Gln | Ala | Ile | Ala | Gly | Phe |
| $AfsB_b$ | Glu | Gln | His | Asp | Ala | Gln | Glu | Val | Gly | Glu | Val | Arg | Ala | Leu | Leu | Ala | Arg | Ser |

```
MboI
GATCGCCCACCAGACCGTGCAGCGCACCGAGTTCGTCTTCCAGCCGGAGCTGGTGGTGCG   60
----.----+----.----+----.----+----.----+----.----+----.----+
 i  a  h  q  t  v  q  r  t  e  f  v  f  q  p  e  l  v  v  r

CGGCTCCACCGCCCAGTGGGTGCCCGGCGGCTGAGGGGACGTACGGGGCGCTTCGTCCGG  120
----.----+----.----+----.----+----.----+----.----+----.----+
 g  s  t  a  q  w  v  p  g  g
                              ApaI
AGCCGCCCGCAATCTCTTGCAGAGGCTTGCGGGCCCTGCTGCCCGGCGCCCAACCCCCTT  180
----.----+----.----+----.----+----.----+----.----+----.----+
                                          SacII-KpnI
GATGTCCGTGGTGTTTCGGGTTCGTGTCCAAAGGGTTGACCGCGGGTACCGCTCGCTCTA  240
----.----+----.----+----.----+----.----+----.----+----.----+
                                           EcoRI
CGGTCTGCTTCGCGACGCTCCTTGCAGTTTTGCTGCAAGAGAATTCAGCCCTCCGCCCCC  300
----.----+----.----+----.----+----.----+----.----+----.----+
                                                   BglI
CGATCAGGAGGCACCACATGGCCCGCAGACTCGCCACCGCGTCCCTAGCCGTGCTGGCGG  360
----.----+----.----+----.----+----.----+----.----+----.----+
                  m  a  r  r  l  a  t  a  s  l  a  v  l  a  a
```

FIG. 11B

```
                                                       SmaI
CGGCCGCCACCGCCCTCACCGCGCCCACACCCGCCGCTGCCGCCCCGCCCGGGGCGAAGG  420
----.----+----.----+----.----+----.----+----.----+----.----+
 a  a  t  a  l  t  a  p  t  p  a  a  a  a  p  p  g  a  k  d

ACGTCACCGCCGTCCTCTTCGAGTGGAAGTTCGCCTCCGTAGCCCGCGCCTGCACCGACA  480
----.----+----.----+----.----+----.----+----.----+----.----+
 v  t  a  v  l  f  e  w  k  f  a  s  v  a  r  a  c  t  d  s
          BglI
GCCTCGGCCCGGCCGGCTACGGATACGTCCAGGTCTCGCCGCCCCAGGAGCACATCCAGG  540
----.----+----.----+----.----+----.----+----.----+----.----+
 l  g  p  a  g  y  g  y  v  q  v  s  p  p  q  e  h  i  q  g

GCAGCCAGTGGTGGACCTCCTACCAGCCCGTCAGCTACAAGATCGCCGGACGGCTCGGCG  600
----.----+----.----+----.----+----.----+----.----+----.----+
 s  q  w  w  t  s  y  q  p  v  s  y  k  i  a  g  r  l  g  d
                     NcoI-SalI
ACCGCGCCGCCTTCAAGTCCATGGTCGACACCTGCCACGCGGCCGGCGTCAAGGTCGTCG  660
----.----+----.----+----.----+----.----+----.----+----.----+
 r  a  a  f  k  s  m  v  d  t  c  h  a  a  g  v  k  v  v  a
```

FIG. 11C

```
                                  SacII
CCGACTCGGTCATCAACCACATGGCCGCGGGTTCCGGCACCGGCACCGGCGGCAGCGCGT  720
----.----+----.----+----.----+----.----+----.----+----.----+
 d  s  v  i  n  h  m  a  a  g  s  g  t  g  t  g  g  s  a  y
                      SmaI
ACCAGAAGTACGACTACCCGGGCATCTGGTCCGGCGCCGACATGGACGACTGCCGCAGCG  780
----.----+----.----+----.----+----.----+----.----+----.----+
 q  k  y  d  y  p  g  i  w  s  g  a  d  m  d  d  c  r  s  e

AGATCAACGACTACGGCAACCGCGCCAACGTCCAGAACTGCGAACTGGTCGGCCTCGCCG  840
----.----+----.----+----.----+----.----+----.----+----.----+
 i  n  d  y  g  n  r  a  n  v  q  n  c  e  l  v  g  l  a  d

ACCTCGACACCGGTGAGCCGTACGTCCGCGACCGCATCGCCGCCTACCTCAACGACCTGC  900
----.----+----.----+----.----+----.----+----.----+----.----+
 l  d  t  g  e  p  y  v  r  d  r  i  a  a  y  l  n  d  l  l

TCTTGCTCGGCGTGGACGGCTTCCGCATCGACGCCGCCAAGCACATGCCCGCCGCCGACC  960
----.----+----.----+----.----+----.----+----.----+----.----+
 l  l  g  v  d  g  f  r  i  d  a  a  k  h  m  p  a  a  d  l
```

FIG. 11D

```
              ___BglI_____
TCACCGCCATCAAGGCCAAGGTCGGCAACGGGAGCACGTACTGGAAGCAGGAGGCCATCC 1020
----.----+----.----+----.----+----.----+----.----+----.----+
 t  a  i  k  a  k  v  g  n  g  s  t  y  w  k  q  e  a  i  h

ACGGCGCGGGCGAGGCCGTCCAGCCCAGCGAGTACCTCGGCACCGGCGACGTCCAGGAGT 1080
----.----+----.----+----.----+----.----+----.----+----.----+
 g  a  g  e  a  v  q  p  s  e  y  l  g  t  g  d  v  q  e  f

TCCGCTACGCCCGCGACCTCAAGCGGGTCTTCCAGAACGAGAACCTGGCCCACCTGAAGA 1140
----.----+----.----+----.----+----.----+----.----+----.----+
 r  y  a  r  d  l  k  r  v  f  q  n  e  n  l  a  h  l  k  n
                                                 SalI
ACTTCGGCGAGGACTGGGGCTACATGGCGAGCGGCAAGTCCGCCGTCTTCGTCGACAACC 1200
----.----+----.----+----.----+----.----+----.----+----.----+
 f  g  e  d  w  g  y  m  a  s  g  k  s  a  v  f  v  d  n  h

ACGACACCGAGCGGGGCGGCGACACCCTCAACTACAAGAACGGCTCCGCCTACACCCTCG 1260
----.----+----.----+----.----+----.----+----.----+----.----+
 d  t  e  r  g  g  d  t  l  n  y  k  n  g  s  a  y  t  l  a
```

FIG.11E

```
CCGGCGTCTTCATGCTGGCCTGGCCCTACGGCTCCCCGGACGTCCACTCCGGCTACGAGT 1320
----.----+----.----+----.----+----.----+----.----+----.----+
  g  v  f  m  l  a  w  p  y  g  s  p  d  v  h  s  g  y  e  f

TCACCGACCACGACGCCGGCCCGCCCAACGGCGGAACCGTCAACGCCTGCTACAGCGACG 1380
----.----+----.----+----.----+----.----+----.----+----.----+
  t  d  h  d  a  g  p  p  n  g  g  t  v  n  a  c  y  s  d  g
                                SacI      NcoI
GCTGGAAGTGCCAGCACGCCTGGCCCGAGCTCTCCTCCATGGTCGGCCTGCGCAACACCG 1440
----.----+----.----+----.----+----.----+----.----+----.----+
  w  k  c  q  h  a  w  p  e  l  s  s  m  v  g  l  r  n  t  a

CCTCCGGGCAGCCCGTCACCAACTGGTGGGACAACGGCGGCGACCAGATCGCCTTCGGCC 1500
----.----+----.----+----.----+----.----+----.----+----.----+
  s  g  q  p  v  t  n  w  w  d  n  g  g  d  q  i  a  f  g  r
SacII
GCGGCGACAAGGCGTACGTCGCCATCAACCACGAGGGCTCCGCGCTGAACCGCACCTTCC 1560
----.----+----.----+----.----+----.----+----.----+----.----+
  g  d  k  a  y  v  a  i  n  h  e  g  s  a  l  n  r  t  f  q
```

FIG.11F

```
      BglI
AGAGCGGCCTGCCCGGCGGCGCCTACTGCGACGTCCAGAGCGGCAGGTCCGTCACGGTCG 1620
----.----+----.----+----.----+----.----+----.----+----.----+
  s  g  l  p  g  g  a  y  c  d  v  q  s  g  r  s  v  t  v  g

GCTCCGACGGCACCTTCACCGCCACCGTCGCCGCCGGCACCGCCCTGGCCCTGCACACCG 1680
----.----+----.----+----.----+----.----+----.----+----.----+
  s  d  g  t  f  t  a  t  v  a  a  g  t  a  l  a  l  h  t  g
 ApaI
GGGCCCGTACCTGCTCCGGCGGCGGAACCGGCCCCGGCACCGGGCAGACCTCCGCCTCCT 1740
----.----+----.----+----.----+----.----+----.----+----.----+
  a  r  t  c  s  g  g  g  t  g  p  g  t  g  q  t  s  a  s  f
                                                BstEII
TCCACGTCAACGCCACCACCGCCTGGGGCGAGAACATCTACGTCACCGGTGACCAGGCCG 1800
----.----+----.----+----.----+----.----+----.----+----.----+
  h  v  n  a  t  t  a  w  g  e  n  i  y  v  t  g  d  q  a  a

CCCTCGGCAACTGGGACCCGGCCCGCGCCCTCAAGCTCGACCCGGCCGCCTACCCGGTGT 1860
----.----+----.----+----.----+----.----+----.----+----.----+
  l  g  n  w  d  p  a  r  a  l  k  l  d  p  a  a  y  p  v  w
```

FIG. 11G

```
GGAAGCTCGACGTGCCGCTGGCCGCCGGAACCCCCTTCCAGTACAAGTACCTGCGCAAGG 1920
----.----+----.----+----.----+----.----+----.----+----.----+
 k  l  d  v  p  l  a  a  g  t  p  f  q  y  k  y  l  r  k  d
   SacII
ACGCCGCGGGGAAGGCCGTCTGGGAGTCCGGCGCCAACCGCACGGCGACCGTCGGCACCA 1980
----.----+----.----+----.----+----.----+----.----+----.----+
 a  a  g  k  a  v  w  e  s  g  a  n  r  t  a  t  v  g  t  t

CCGGCGCCCTCACCCTCAACGACACCTGGCGCGGCTGACCCCGCCCCCATCGGCCCGGCG 2040
----.----+----.----+----.----+----.----+----.----+----.----+
 g  a  l  t  l  n  d  t  w  r  g
         SacII
CCCGCCTCCCCGCGGACGCCGGGCCGCTGCCGCACCCGCCCCGCGAACCCCGCCCGGCGG 2100
----.----+----.----+----.----+----.----+----.----+----.----+

CCCCCGCCCCCGAAGGAGACCCGTCCCCGTGCGACGGACCACCATCCTCGCGGTGAGTCT 2160
----.----+----.----+----.----+----.----+----.----+----.----+
                                 m  r  r  t  t  i  l  a  v  s  l
```

FIG.11H

```
CGGCCTGTGCGCCGCCCTCACCGCCACCCTCCCGGCCACCGCCGACACCCCCGACGCCCC 2220
----.----+----.----+----.----+----.----+----.----+----.----+
 g  l  c  a  a  l  t  a  t  l  p  a  t  a  d  t  p  d  a  p
    BglI                                          TaqI
GGCCGCGCGGGCCACCGCCGCCGAGGACACCGCCGAGGCCGTCTGGCTCGA  2271
----.----+----.----+----.----+----.----+----.----+-
 a  a  r  a  t  a  a  e  d  t  a  e  a  v  w  l
```

SAF POLYPEPTIDE, GENE CODING THEREFOR, SAF PROMOTER AND EXPRESSION METHODS FOR EXPRESSING FOREIGN DNA SEQUENCES IN STREPTOMYCES

CROSS-REFERENCE TO RELATED APPLICATION

The present application is a continuation-in-part of U.S. application Ser. No. 354,265, filed May 19, 1989, the entire contents of which are hereby incorporated by reference.

FIELD OF THE INVENTION

The invention is in the field of biotechnology. More particularly, it relates to a new polypeptide increasing production of extracellular enzymes, DNA that codes for the polypeptide, a recombinant vector that includes the DNA, and a host organism transformed with the recombinant vector that includes the DNA encoding the polypeptide. Furthermore, the invention is directed to the promoter sequence of the gene encoding the new polypeptide. The present invention further relates to Streptomyces expression systems and methods for expressing foreign DNA sequences in Streptomyces and for secreting to the surrounding medium polypeptides and proteins coded for by those foreign DNA sequences.

BACKGROUND OF THE INVENTION

The Streptomyces are well known producers of a variety of extracellular enzymes including proteases, phosphatases, xylanases, cellulases, amylases, lipases and nucleases.

In addition, members of the genus Streptomyces produce a large number of antibiotics, pigments and other secondary metabolites and have a complex pattern of differentiation resulting in the formation of spores. In batch cultures of Streptomyces there is usually a coincidence in the production of extracellular enzymes and the onset of antibiotic production and pigment biosynthesis and sporulation. All of these processes are repressed by nutritional conditions favoring high growth rates and are derepressed by starvation of P, C or N sources. It is likely that enzyme secretion, formation of secondary metabolites and differentiation are completely independent but respond to similar triggering mechanisms.

Several genes of Streptomyces encoding extracellular enzymes have been cloned. These include agarase from *Streptomyces coelicolor,* endoglycosidase H from *Streptomyces plicatus,* xylanase from *Streptomyces lividans,* alpha-amylase from *Streptomyces hygroscopicus,* cellulase from *Strep. spA*2, beta-galactosidase from *Strep. lividans* and beta-lactamases from *Strep. cacaoi, badius* and *fradiae.*

However, the regulatory mechanisms which control expression of these genes are virtually unknown. In addition to specific regulatory mechanisms, such as induction of amylase by dextrins or maltotriose and carbon metabolite regulation of amylase or agarase, general mechanisms of derepression of several extracellular enzymes are likely to occur since simultaneous production of several polymeric-substrate degrading enzymes has been observed in *Streptomyces* following a nutritional down-shift. Such transacting regulatory genes have been found in *Bacillus subtilis* (J. BACTERIOL. 169:324-333,1987), *Bacillus natto* (J. BACTERIOL. 166:20-28,1986), and *Bacillus licheniformis.*

Positive regulatory genes affecting enzyme synthesis and/or secretion might be cloned by searching for increased secretion of extracellular enzymes in a poor secretory strain such as *S.lividans.*

Systems for expressing foreign DNA sequences in Streptomyces have previously been described in, for example, EP 148,552 and WO 88/07079. These systems use the endogenous promoters of extracellular enzymes produced by Streptomyces.

OBJECTS OF THE INVENTION

A principal object of this invention is to provide the cloning and characterization of a newly isolated gene, hereinafter referred to as saf (secondary metabolism activation factor) gene, encoding a new amino acid polypeptide (hereinafter referred to as SAF polypeptide). The SAF polypeptide modulates directly or indirectly expression of the genes for extracellular enzymes in Streptomyces by interacting with the control region of the structural genes for the extracellular enzymes.

A second aspect of the invention is DNA units or fragments comprising nucleotide sequences that upon expression encode the above described SAF polypeptide.

A third aspect of the invention is cloning vehicles (vectors) that include the above described DNA.

A fourth aspect of the invention is host organisms or cells transformed with the above described cloning vehicles; thereby resulting in increased production of extracellular enzymes or of a desired heterologous polypeptide.

A fifth aspect of the invention is a process for the preparation of extracellular enzymes or of a desired polypeptide by culturing a transformed host organism according to the present invention and recovering the product from the culture broth.

Still another aspect of the invention is the promoter of the saf gene.

It is yet another aspect of the present invention to produce cloning vehicles (vectors) which include the promoter of the saf gene operatively linked to the secretion signal region of an endogenous extracellular enzyme, both of which are operatively linked to a foreign DNA sequence, as well as host organisms or cells transformed with such cloning vehicles, thereby resulting in expression and secretion of the foreign polypeptide encoded by the foreign DNA sequence.

Another aspect of the present invention is the integration of such a cloning vehicle carrying a foreign DNA sequence into the chromosomal DNA of Streptomyces. In a preferred embodiment, an expression vector containing the saf gene will also be incorporated into such transformed organisms.

These and other objects of the invention will be described in more detail in the further specification.

SUMMARY OF THE INVENTION

A DNA fragment from *Streptomyces griseus ATCC* 10137 has been isolated that encodes a gene saf (secondary metabolism activation factor) which is involved in a common control mechanism for at least five extracellular enzymes in *S.lividans* and *S. coelicolor.* The saf gene is present in all Streptomyces tested, which suggests that this gene must have an important role in metabolism. Indeed, a DNA fragment containing a similar gene to saf has been cloned by us from *Streptomyces griseus*

IMRU 3570, the candicidin producer strain. In some Streptomyces. e.g., *S. lividans* and *S.lactamdurans*, the hybridization pattern suggests that the saf gene is present in several copies in the chromosomal DNA.

This is the first example of a gene involved in production of extracellular enzymes and sporulation in Streptomyces.

The saf gene encodes a polypeptide of 113 amino acids (the SAF polypeptide); in vitro transcription-translation studies in *E.coli* showed that a protein of the correct size, about 15000 dalton, is formed. The SAF polypeptide has a strong positive charge (18 positively charged amino acids) and does not show a composition typical of a peptide leader or a transmembrane protein and, therefore, a direct effect on protein excretion appears to be unlikely. The positively charged protein may easily interact with DNA. In fact, a DNA-binding domain typical of several regulatory proteins (ANN. REV. BIOCHEM. 53:293-321, 1984) is observed in the SAF polypeptide.

The saf promoter has unexpectedly been found to be more potent than natural promoters of extracellular enzymes. For example, the amylase gene expresses much greater quantities of amylase when the saf promoter is substituted for the natural amylase promoter. Thus, the saf promoter can be used to enhance the expression of any endogenous polypeptide or protein in place of that protein's natural promoter.

The SAF polypeptide has a pleiotropic effect, i.e., an effect affecting more than one pathway, on extracellular enzymes, on pigment production and on differentiation. In accordance with the invention, an increased production of endogenous (extracellular) proteins is achieved.

Broadly, the saf gene and corresponding polypeptide can be used to increase expression in Streptomyces of selected heterologous proteins by inserting the gene coding for the desired protein into a suitable cleavage site of the gene coding for an extracellular enzyme, the expression of which is enhanced by SAF, or a part thereof, transforming a Streptomyces host containing the saf gene with the recombined gene, and culturing the transformed bacteria to excrete the selected protein or portion thereof. Preferably, the heterologous DNA, under control of the saf promoter, is inserted (integrated) into the chromosomal DNA and an expression vector containing DNA encoding the SAF polypeptide is concurrently inserted. The expression vector need not be integrated into the chromosomal DNA.

Pleiotropic genes affecting biosynthesis of antibiotics and differentiation in Streptomyces have been reported. A gene afsB which positively controls the production of A-factor, actinorhodin and prodigiosin in *Streptomyces coelicolor* and *Streptomyces lividans* was cloned from *S.coelicolor* A3(2) (Horinouchi et al., J. BACTERIOL. 155:1238-1248, 1983).

The saf gene is different from the afsB and in fact they have opposite effects on production of actinorhodin. They have in common that they have an amino acid sequence typical of DNA-binding proteins. Both afsB and saf genes have promoters without the −10 and −35 consensus sequences and are bounded by potential translational regulatory signals and by strong stem and loop structures that may act as transcriptional terminators (Horinouchi et al., J. BACTERIOL. 168:257-269, 1986). If the transcription forms a very stable loop, binding of the ribosomes will be precluded. Such attenuation-like mechanisms of control of gene expression have been found to modulate control of antibiotic resistance genes in Streptomyces (Horinouchi et al., PROC. NATL. ACAD. SCI. USA 77:7079-7083, 1980). Since the saf gene might be considered as a "master" gene which switches on a variety of genes for enzyme excretion, its expression is probably tightly controlled in the cell. The enzymes stimulated by the saf gene are all involved in the degradation of complex polymers and therefor we speculate that this gene is part of a global regulatory system involved in the search for alternative nutrient sources, as suggested also in Bacillus (Henner at al. J. BACTERIOL. 170:296-300, 1988).

BRIEF DESCRIPTION OF THE DRAWINGS

FIG. 6 Nucleotide sequence of the 1 kb BglII fragment of pULAD3 and deduced amino acid sequence of the saf gene product. The second putative ATG initiation codon is underlined. Inverted complementary repeat sequences are shown by convergent arrows. The wavy line indicates the amino acid sequence similar to DNA-binding domains of known DNA-binding proteins. The relevant restriction sites are shown. The nucleotides are numbered starting with the BglII site (numbers on the right).

FIG. 7 Comparison of a region from the deduced amino acid sequence of the saf gene product with DNA-binding domains in known DNA-binding proteins. Data were taken from Pabo and Sauer (Pabo et al. ANN. REV. BIOCHEM. 53:293-321, 1984) and Horinouchi and Beppu (Horinouchi et al., GENETICS OF INDUSTRIAL MICROORGANISMS, p.41 Pliva, Zagreb, Yugoslavia, 1986).

FIG. 11 FIGS. 11A to 11H show the complete sequence of nucleotides and inferred sequence of amino acids of the amylase gene of *S.griseus.* It is thought that cut BstEII is the optimum place for fusion of a foreign gene.

(Δ) MM+starch (1%)+thio (□) MM 1 mMP+starch (1%)+thio (■) MM without phosphate+starch (1%)+thio (○) MM+starch (1%)+thio+IPTG The bottom right-hand panel shows the production values of plasmid pULVD10 as compared with pULTV1, S.lividans and pULTV100 in the best production media. (×) *S.lividans* (pIJ699) in MM without phosphate +1% starch +thio; (●) pULTV1 in the previous medium; (−) pULTV100 in the previous medium; and (Δ) pULVD10 in MM 1 mMP+1% starch+thio.

Figure 14:
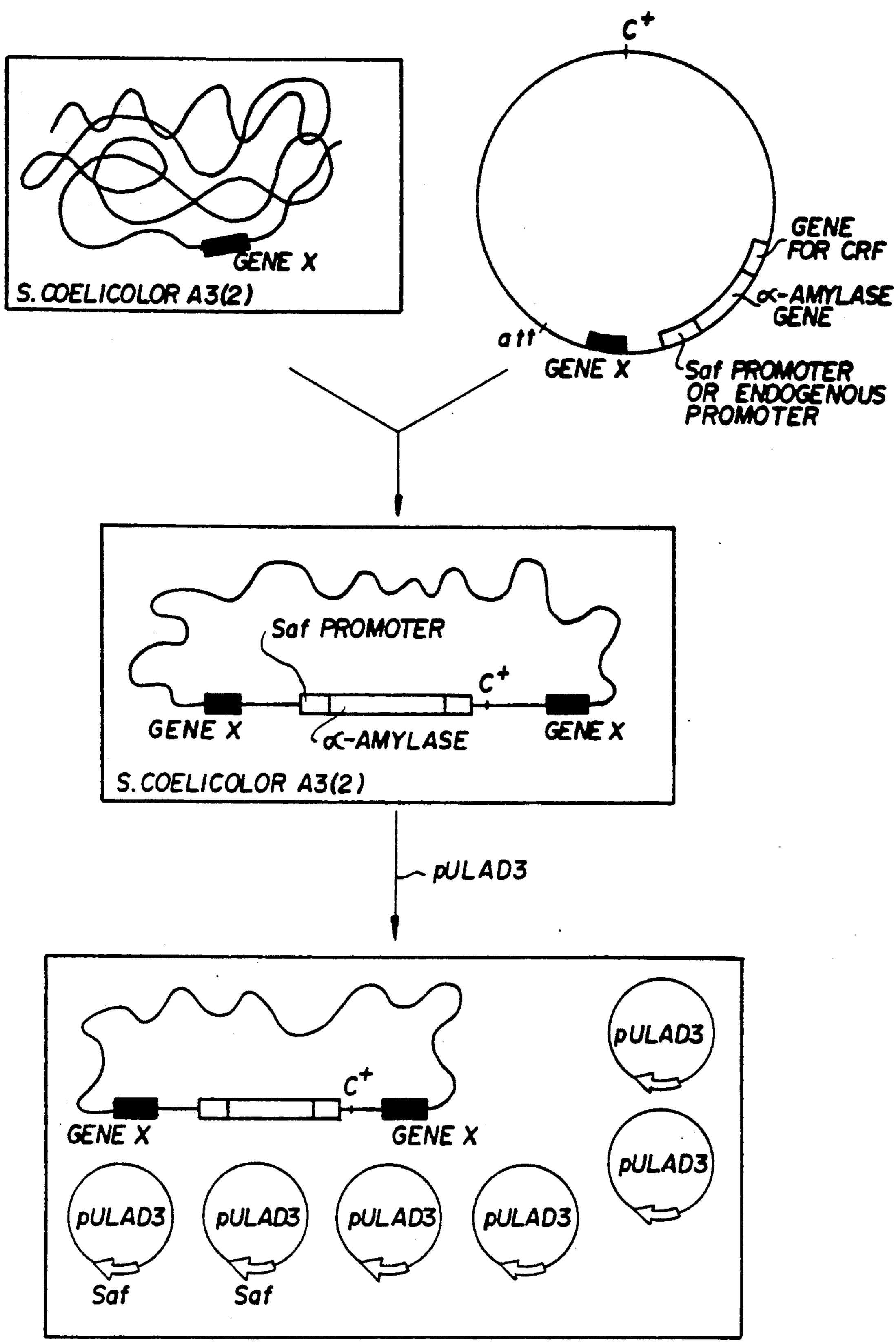

FIG. 14 A schematic representation of the construction of a recombinant Streptomyces cell containing a chromosomal gene producing a fusion protein including the CRF molecule and plasmids containing DNA coding for the SAF polypeptide.

DESCRIPTION OF PREFERRED EMBODIMENTS

The work described herein was performed employing the following materials and methods.

Bacterial strains and plasmids. The Streptomyces and *E.coli* strains used in this study are listed in Table 1. Plasmids and phages are in Table 2.

Media and culture conditions. Streptomyces strains were grown in R2YE, minimal medium (MM), TSB (Difco) or YEME supplemented with 34% sucrose and 5 mM $MgCl_2$ (Hopwood et al., Genetic manipulation of Streptomyces. A LABORATORY MANUAL. The John Innes Foundation, Norwich, U.K., 1985). Streptomyces strains were grown in triple baffled flasks at 28° C. in a rotary shaker with an agitation of 220 rpm.

*E.coli* strains were grown in Luria Broth (LB) (Miller et al., EXPERIMENTS IN MOLECULAR GENETICS, p.433. Cold Spring Harbor Laboratories, New York, 1972) or Luria Agar (LA) at 37° C.

Enzyme assays in plates. Alkaline phosphatase (AP) assays for Streptomyces were carried out in PRMM medium (MM) without glucose and containing a reduced level [lmM] of phosphate supplemented with 30 mcg/ml of 5-bromo-4-chloro-3-indolylphosphate-p-toluidine (XP). Colonies producing AP were blue and those unable to produce it were white. For E.coli, B-XP medium was used (containing per liter: 10 g bactopectone, 12 g Trisma-base, 10 g NaCl, 20 g Difco agar, pH 7.5 and 40 mcg/ml of XP).

Amylase activity of Streptomyces colonies was assayed on MM (without glucose) supplemented with 1% starch. After 3 days of growth, the plates were exposed to iodine vapor. Zones of clearing around the colonies are due to starch degradation. Lipase activity was measured by growing the Streptomyces in MM supplemented with 2% (w/v) olive oil, 0.5% (w/v) Tween 80 and 0.5% (w/v) Tween 20. After 3 days of growth the plates were flooded with 1 ml of 1M $CaCl_2$. The lipase production was observed as a precipitate of $Ca^{2+}$-fatty acid et al., FERMENT. TECHNOL. 64:363–371, 1986). Protease activity was assayed in MM (without glucose) supplemented with 0.5% casein and 10 mM $CaCl_2$. The enzyme activity was detected as zones of clearing around the colonies.

Agarase activity of *S.coelicolor* was assayed in MM without glucose by flooding the plates with Gram's iodine solution. Beta-galactosidase activity was observed as a blue color of the colonies growing on MM without glucose, and supplemented with X-gal (36 mcg/ml) and IPTG (10 mcg/ml).

DNA isolation. Total DNA from Streptomyces was prepared as described by Hopwood et al. (Hopwood et al., A LABORATORY MANUAL, The John Innes Foundation, Norwich, U.K., 1985). Plasmid DNA from Streptomyces or *E.coli* was isolated following the method of Kieser (Kieser et al., PLASMID 12:19–36, 1984).

Cloning procedures. Ten mcg of *S.griseus* ATCC 10137 chromosomal DNA and 0.5 mcg of pIJ702 were totally digested with BglII, and ligated for 12 h at 14° C. using T4 DNA ligase. The ligation mixture was used directly for transformation. Subcloning of DNA fragments was carried out by digesting 1–2 mcg of plasmid DNA with adequate restriction enzyme(s) and the reaction products were separated by gel electrophoresis in low melting point agarose (LMPA). The required DNA bands were extracted using the CTAB-assisted method (Langridge et al., ANAL. BIOCHEM. 103:264271, 1980).

Transformation methods. Streptomyces strains were transformed as described by Hopwood et al. (Hopwood et al., A Laboratory Manual, The John Innes Foundation, Norwich, U.K., 1985). After transformation, protoplasts were plated on R2YE medium, and allowed to regenerate for 15–20 h at 30° C. Then, 1 ml of an aqueous solution of thiostrepton (300 mcg/ml) was poured over the plates, dried for 1 or 2 h and incubated for 2 or 3 days more. Transformants were replicated to PRMM medium containing thiostrepton (50 mcg/ml) and XP (30 mcg/ml).

Transformation of *E.coli* was done according to Cohen et al. (PROC. NATL. ACAD. SCI. USA 69:2110–2114, 1972). Transformants were selected on plates containing ampicillin (200 mcg/ml). When required, X-gal (36 mcg/ml) and IPTG (10 mcg/ml) were added to LA plates.

Hybridization studies. Transfer of DNA from agarose gels to nitrocellulose filters and hybridizations were carried out as described by Hopwood et al. (A Laboratory Manual, The John Innes Foundation, Norwich, U.K., 1985). The 7.2 Kb BglII fragment from plasmid pULAD1 and the 1 Kb BglII fragment from plasmid pULAD3 were used as probes. Hybridizations were performed at 70° C. for 24 h. The filters were washed twice for 30 min in 2 g SSC, 0.1% SDS and then twice again for 30 min in 0.2 g SSC, 0.1% at 70° C.

Nucleotide sequence analysis. The nucleotide sequence was determined by the chain termination method of Sanger et al. (PROC. NATL. ACAD. SCI. USA 74:5463:5467, 1977). The DNA fragments were subcloned into M13mp10 and M13mp11 to obtain the insert in either orientation. Ligation mixtures were transfected into competent E.coli JM103 cells and white plaques were screened for selection of inserts. The sequencing was performed in both strands using Amersham International plc. (U.K.) and Sequenase (United States Biochemical Corporation, USA) kits. All the fragments were sequenced using dGTP, but dITP was used instead of dGTP when needed. Reaction mixtures were separated on 6% or 8% polyacrylamide sequencing gels which were then exposed to X-ray film for autoradiography.

Promoter cloning. Fragments with transcription initiation activity were selected by using the multicopy promoter-probe plasmid pIJ486 (Ward et al., MOL. GEN. GENET. 203:468–478, 1986). Kanamycin (Km) resistant transformants were isolated by replication of colonies to MM containing 15 mcg/ml of Km.

In vitro transcription-translation. Plasmids pULAD300 and pUC19 were transcribed and translated using the prokaryotic DNA directed translation kit from Amershan International plc. L-($^{35}$S) methionine was used as radioactive label. 12.5% polyacrylamide gels containing sodium dodecyl sulphate were used to analyze the labelled proteins.

Modes of Carrying Out the Invention

The following detailed description will illustrate the invention:

Alkaline phosphatase production by different Streptomyces

The alkaline phosphatase production in several solid media of ten different Streptomyces strains (listed in Table 1) was assayed. *S.griseus* IMRU 3570 and *S.griseus* ATCC 10137 were the best producers in all the media assayed. The best solid medium for alkaline phosphatase production was PRMM (containing 30 mcg/ml XP). In this medium, *S.griseus* IMRU 3570 and *S.griseus* ATCC 10137 showed a deep blue color after 48 h of growth. *S.lividans* 1326 and *S.coelicolor* JI 2280 were poor alkaline phosphatase producers: after 90 h of growth on PRMM containing XP only a weak blue color can be observed.

Cloning of a Gene Involved in Alkaline Phosphatase Production

Figures 1, 10:
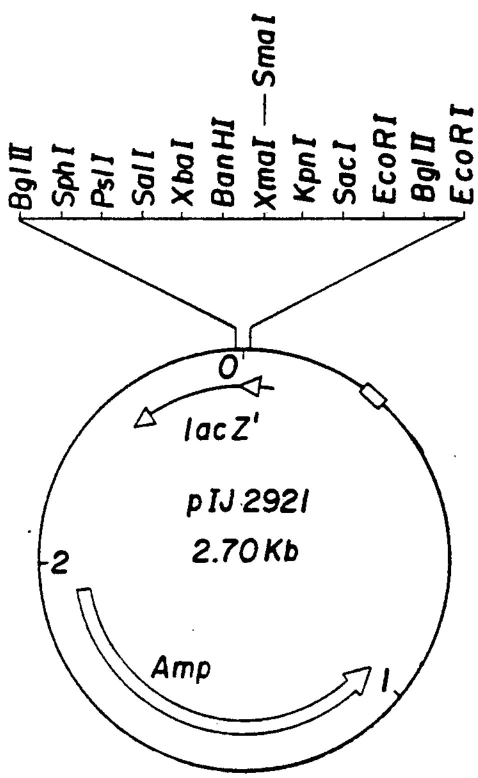
FIG. 1 Restriction maps of chromosomal DNA fragments from *S.griseus* ATCC 10137 clones in the BglII site of pIJ702 that carry the genetic determinant for alkaline phosphatase hyperproduction.
FIG. 10 Plasmid pIJ2921.

Total DNA from *S.griseus* ATCC 10137 was digested with BglII, ligated to BglII-digested pIJ702 and the ligation mixture introduced by transformation into *S.lividans* 1326 protoplasts. The transformants were replicated to PRMM containing thiostrepton (50 mcg/ml) and XP (30 mcg/ml). One deep blue colony was found among 2,800 melanine negative transformants of *S.lividans*. The deep blue colony contained a pIJ702 derivative carrying a 7.2 kb BglII insert which was named pULAD1 (FIG. 1).

Plasmid pULAD1 was unstable in *S.lividans* and upon retransformation gave rise to white and blue colonies. All the blue colonies contained the original pULAD1 and the white ones contained deleted forms of pULAD1 that were no longer studied. Since the instability might be caused by the large size of the insert in a plasmid such as pIJ702, which is known to have a BglII fragment of plasmid pIJ699 (Kieser et al. GENE 65:83–91, 1988). Two plasmids, pULAD100 and pULAD100 were obtained with the insert in opposite orientation. Both plasmids were stable and the gene was expressed in both orientations in *S.lividans*.

Localization of the Saf Gene

The 7.2 Kb BglII fragment was partially digested with Sau3AI, and ligated to BglII-digested pIJ702. The ligation mixture was transformed into *S.lividans* protoplasts and transformants were replicated to PRMM containing XP. Plasmid DNA was isolated from several blue colonies. Four small plasmids, pULAD2, pULAD3, pULAD16 and pULAD18, carrying the determinant for alkaline phosphatase production, were studied in detail; they were stable, retransformed *S.lividans* protoplasts, and carried inserts of 2.4, 1, 2.1 and 1.9 Kb (FIG. 1), respectively. The plasmid pULAD3 has the smallest insert (1 Kb) which can be rescued with BglII. When introduced into *S.lividans.* pULAD3 (deposition number I-859 on 19.05.89 with CNCM (Collection Nationale de Cultures de Micro-organismes, 28 rue du Docteur Roux, F75724 Paris Cedex 15, France) under the Budapest Treaty and Rule 28 EPC) increased alkaline phosphatase production like pULAD1.

Hybridization With Chromosomal DNA of Several Streptomyces

Total DNA from *S.griseus* ATCC 10137 digested with BamHI or BglII were hybridized to the 7.2 Kb BglII fragment from pULAD1 labelled by nick translation with (32p) dCTP. A 7.2 Kb BglII fragment homologous to the probe was present in *S.griseus* ATCC 10137 DNA digested with BglII, as expected. There was an internal BamHI site in the fragment that resulted in two clear hybridization bands (of 7.9 Kb and 9.4 Kb) when total DNA was digested with BamHI.

Figures 2A, 2B:
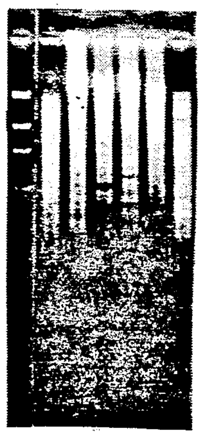
FIG. 2 Southern hybridization analysis of homology between the 1 kb BglII fragment of pULAD3 and genomic DNA of other Streptomyces species. (A) DNA fragments generated by BamHI digestion of genomic DNAs (Lanes 2 to 7). (B) Hybridization of DNAs shown in panel A, with the 1 kb fragment as the probe. Lanes: 1, HindIII digest of DNA giving fragments of 23, 9.59, 6.68, 4.29, 2.28, 1.94 and 0.58 kb; 2, *S.lactamdurans;* 3, *S.acrimycini:* 4, *S.coelicolor* 1157; 5, *S.griseus* 2212; 6, S.griseus 3570; 7, *S.lividans* 1326.

To study if the same gene was present in other Streptomyces, total DNA from *S.acrimycini, S.coelicolor* 1157, *S.griseus* 212, *S.griseus* 3570, *S.lividans* 1326 and *S.lactamdurans* NRRL were digested with BamHI and hybridized with the 1 Kb BglII fragment of pULAD3 as a probe. Hybridization with a 9.5 Kb common band was observed in the first four strains of Streptomyces cited above, whereas 4 and 5 weak hybridization bands were observed in the DNA of *S.lividans* and *S.lactamdurans,* respectively (FIG. 2). In addition, hybridization was also observed with the DNA of *S.albus* G, *S.coelicolor* JI 2280, *S.clavuligerus* NRRL 3585 and *S.fradiae* ATCC 10475. No further attempts were made to characterize the hybridizing bands.

Lack of Complementation of *E.coli* Pho-mutants

Complementation of the *E.coli* phoA mutants E15 and AW1046 was tried to check if we had cloned the alkaline phosphatase structural gene from *S.griseus* ATCC 10137. The 7.2 Kb BglII fragment from pULAD1 and the 1 Kb BglII fragment from pULAD3 were subcloned separately in both orientations in BamHI-digested pUC19. All these plasmid constructions were verified in *E.coli* JM103 cells and then used to transform *E.coli* E15 (Sarthy et al., J. BACTERIOL 145:288–292, 1981) and *E.coli* AW1046. No blue colonies in B-XP were found suggesting that the complete structural gene for alkaline phosphatase is not present in the 7.2 Kb fragment of *S.griseus* or that it is not expressed in *E.coli.* The structural gene for alkaline phosphatase (phoA) or *Bacillus licheniformis* (Hullett, F. M., J. BACTERIOL. 158:978–982, 1984) did not hybridize with the cloned 1 Kb fragment (data not shown).

In addition, the phoB (regulatory) *E.coli* mutant H2 (Kreuzer et al., GENETICS 81:459-468, 1975) was not complemented by either the 1 kb BglII fragment of pULAD3 or the 7.2 BglII fragment of pULAD1.

Overproduction of Other Extracellular Enzymes

Figure 3A:
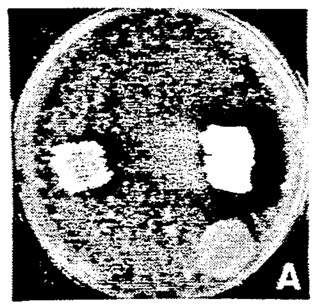
FIG. 3 Assays on Petri dishes of protease (A), amylase (B) and lipase (C) activities of *S.lividans* transformed with (right).
Figure 3B:
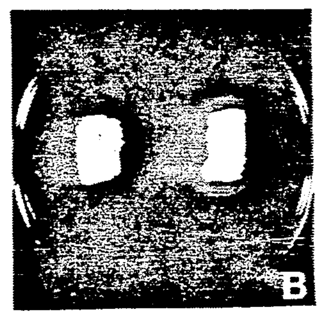
Figure 3C:
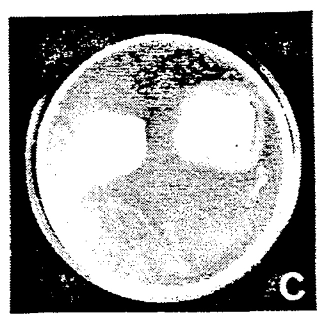

When pULAD3 was used to retransform *S.lividans* protoplasts, a clear delayed pigmentation and sporulation was observed. These pleiotropic effects prompted us to study the role of this gene in protein secretion or in control of gene expression. As shown in FIG. 3, several extracellular enzymes, including amylase, protease and lipase, were overproduced by *S. lividans* transformed with pULAD3. The β-galactosidase production was also increased and its production started about 24-30 h earlier than in untransformed S.coelicolor. Due to the pleiotropic effects of the cloned gene on extracellular enzymes, on pigment production and on differentiation, this gene was named saf (secondary metabolism activation factor).

Gene Dosage Effect

The copy number of pIJ702 is estimated to be 100 to 200 per chromosome. Although the exact copy number of pULAD3 was not determined, the intensity of both pIJ702 and pULAD3 bands suggested a similar copy number.

Figure 4A:
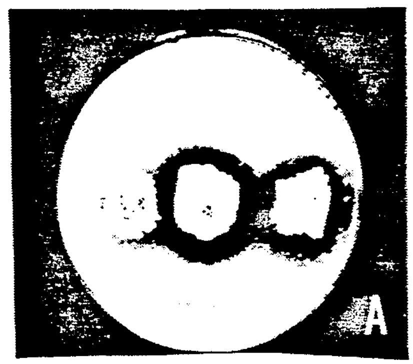
FIG. 4 Gene dosage effect on the expression of the saf gene. Production of protease (A) and amylase (B) by *S.lividans* transformed with pIJ702 (left), *S.lividans* transformed with pULAD3 (middle) and *S.lividans* transformed with pULAD30 (right).
Figure 4B:
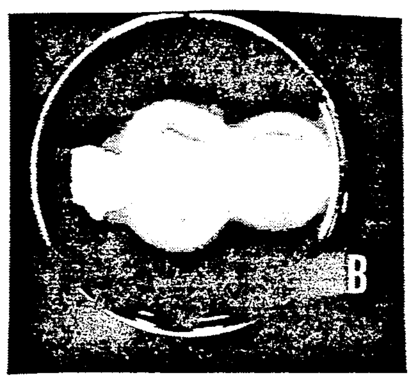

To study the gene dosage effect we subcloned the 1 kb BglII fragment of pULAD3 into the BamHI site of the low copy number plasmid pIJ61 (3 to 4 copies per ce]1) (Hopwood et al. A Laboratory Manual. The John Innes Foundation, Norwich, U.K.). This new plasmid was named pULAD30. FIG. 4 shows that the production of extracellular enzymes by *S.lividans* transformed with pULAD30 clearly decreased with respect to *S.lividans* carrying pULAD3. In addition, *S.lividans* carrying pULAD30 showed a similar pigment production and sporulation pattern as untransformed *S.lividans.*

Expression in *E.coli* and Trimming Down of the Gene

Although pho mutants of *E.coli* were not complemented by the saf gene, we observed that the 1 kb BglII insert of pULAD3, when subcloned in one direction in pUC19 (plasmid named pULAD300) was expressed in *E.coli* causing abnormal morphology when grown on solid media, but it was not expressed when inserted in opposite orientation (plasmid pULAD301). Plasmid pULAD300 contains the ORF (see below) downstream from the lacZ promoter. These results suggest that the saf gene is expressed in *E.coli* from the lacZ promoter present in pUC19.

In-vitro transcription-translation in *E.coli* assays (with pULAD300) were carried out and the products of the reaction were loaded in a 12.5% polyacrylamide gel. A band of MW 15000 was present in the lane corresponding to pULAD300 which was absent in the control pUC19 lane.

Figure 5:
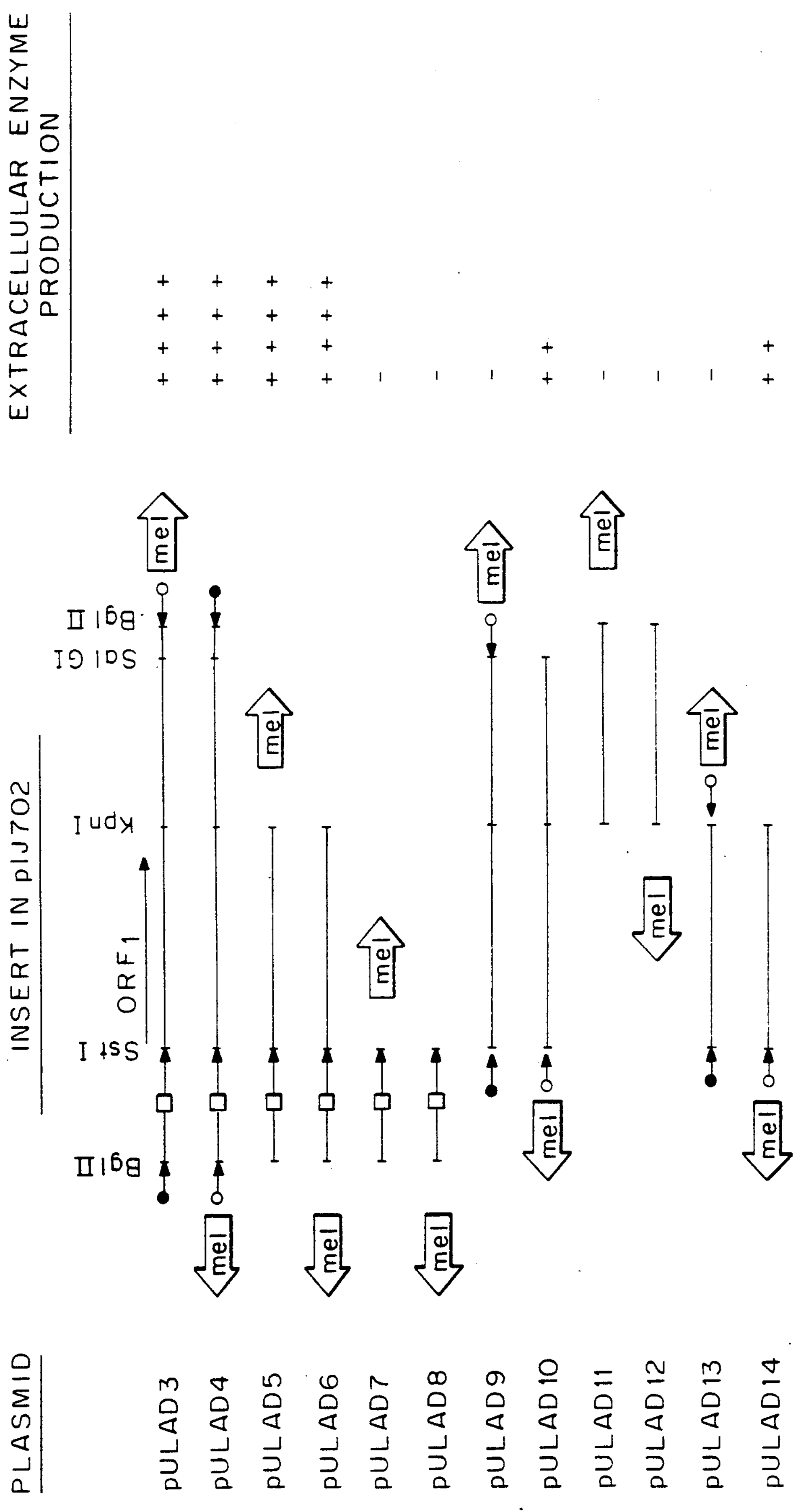
FIG. 5 Trimming down of the saf gene. The 1 kb BglII fragment of pULAD3 was used as starting material. Extracellular enzyme production for all the plasmid constructions was measured on solid media plates as indicated in the description: −, wild type producer; ++, +++and ++++ indicate different rates of hyperproduction. Short open arrows indicate the localization and direction of the transcription of the tyrosinase gene (mel) in plasmid pIJ702. Closed circles (•→) indicate the mel gene promoter; open circles (◦→) represent a putative clockwise promoter activity in pIJ702 and open squares (□→) indicate the saf promoter. The direction of transcription is shown by arrows. The ORF1 corresponds to the saf reading frame deduced from nucleotide sequence data (see FIG. 6).

To locate precisely the saf gene it was decided to continue the splitting of the 1 Kb fragment of plasmid pULAD300. In these trials there was exploited the existence of unique cut sites for restriction enzymes SstI (nt 216), KpnI (nt 648) and SalGI (nt 936) within the 1 kb fragment. The different sub-fragments from the 1 kb insert of pULAD300 were cloned in a first step into pIJ2921, a derivative of pUC18 containing a modified polylinker flanked with BglII sites (see FIG. 10) and then rescued with BglII cohesive ends and cloned into BglII-digested pIJ702. Alkaline phosphatase, amylase and protease production was studied in Streptomyces lividans with all plasmid constructions. The results of these studies appear in outline form in FIG. 5 and the following conclusions have been extracted from their interpretation:

1. The 1 kb fragment contains the complete saf gene, including its own promoter, since it was expressed at a similar level in both orientations of plasmid pIJ702 (plasmid pULAD3 and pULAD4).
2. The saf gene seems to be located in the 648 nucleotides BglII-KpnI fragment (plasmids pULAD5 and pULAD6).
3. Fragment SstI-KpnI (432 nucleotide) seems to contain the genetic determinant for extracellular enzyme hyperproduction, but appears to have lost its promoting region, since it was expressed only in one orientation (plasmid pULAD10 and pULAD14), but not on the opposing one (plasmid pULAD9 and pULAD13).
4. The 215 nucleotides fragment BglII-SstI contains the saf gene promoter region.
5. All the effects on extracellular enzymes and on differentiation were kept or lost together, indicating that a single genic product was responsible for the action on all the enzymes.
6. A surprising aspect was the lack of expression of fragment SstI-KpnI (saf gene without promoter), starting from the tyrosinase promoter of the mel-gene present in pIJ702, which nevertheless was expressed in the opposite direction (clockwise direction). This finding implied that there was a fragment with promoter activity located before gene mel, and at the BglII cloning site (Bernan et al., GENE 37:101-110, 1985). Although such finding has not been published, it has occasionally been mentioned by some authors (Gil and HopWood, GENE 25:119-132, 1983).

The possibility of a functional ORF in reverse direction (from KpnI—SstI) was discarded, for several reasons:

A. Such ORF was not detected when the nucleotide sequence was analyzed.
B. If such ORF were to exist, it would be clear that it would have to carry its own promoter, since fragment BglII-KpnI (nt 1 to nt 648) was expressed in both directions (plasmids pULAD5 and pULAD6). It did not make sense then, that the KpnI—SstI fragment which would carry the promoter in the KpnI zone could only express itself in one direction.
C. Expression in *E.coli* always took place when the promoter lacZ was in favor of (before) the proposed ORF, and never in the opposite direction.

Promoter Activity of ORF1 Upstream DNA Fragment

In order to confirm the existence of a promoter in the BglII—SstI fragment, as could be inferred from previous experiments, said fragment was subcloned in the probe vector for pIJ486 fragments L(Ward et at. MOL. GEN. GENET. 203:468-478, 1986), which carries the gene that codifies for aminoglycoside phosphotransferase (neo), without its promoter. The expression of this gene made *S.lividans* resistant to kanamycin and neomycin. When the fragment was subcloned in pIJ486 (with the SstI end next to neo gene), plasmid pIJ484::216 was created. It was observed that *S.lividans* transformed with pIJ486::216 grows in MM with over 100 mcg/ml Km while *S.lividans* transformed with pIJ486 did not grow in MM supplemented with 5 mg/ml Km. These results indicated that such fragment had promoter activity and supported the proposed ORF.

Figure 8A:
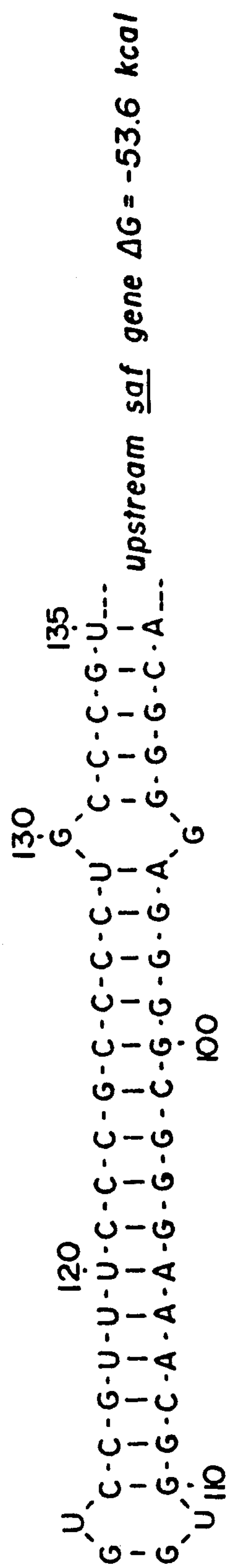
FIG. 8 (parts A–C) Repeated nucleotide sequences "upstream" and "downstream" of the saf gene.
Figure 8B:
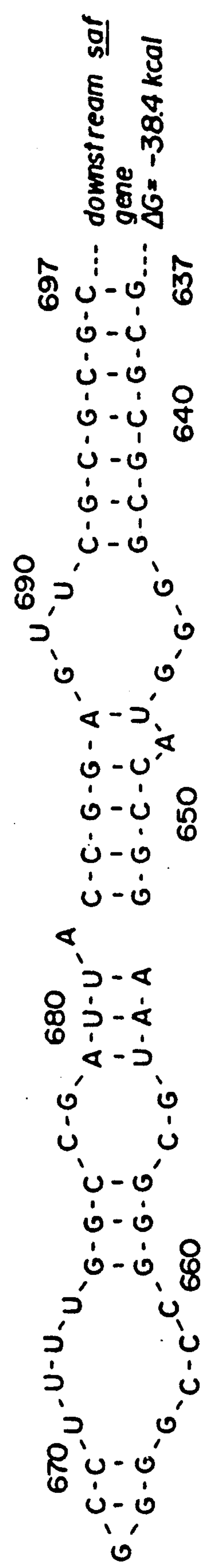
Figure 9:
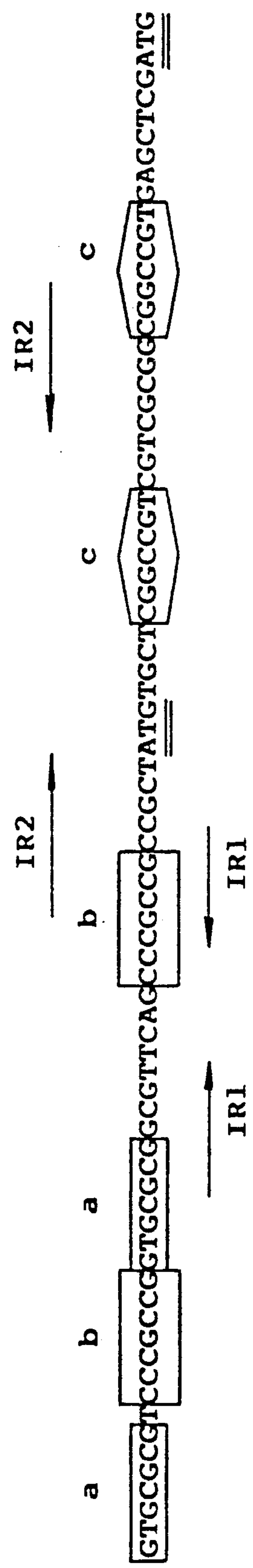
FIG. 9 Repeated groups of nucleotides present in the saf gene.

Other considerations that were deduced from the nucleotide sequence and probable ORF, included:

1. Gene saf was surrounded by two regions with inverted and complementary repeated sequences, which could form in mRNA very stable bonds $\Delta G = -38.4$ Kcal, being gene saf, nt 637–697) (FIG. 8).
2. The sequenced fragment contains a high G+C percentage, as is usual in *Streptomyces* genes.
3. Before gene saf, between ATG (nt 219) and the repeated upstream structures, there is a very interesting nucleotide region: there are three pairs of repeated nucleotides (each one with 7 nt) (FIG. 9). It is very likely that this region, especially the promoter zone, plays a very important part in the regulation of gene saf expression.
4. It is worth mentioning that the SAF protein contains 18 net positive charges. From a hypothetical perspective, this could imply the existence cf a much greater affinity for DNA. Even in the deduced amino acid sequence, a very similar region to the domains of DNA-linking proteins can be observed (Pabo and Sauer, 1984) (FIG. 7).

Nucleotide Sequence of the Saf Gene

The nucleotide sequence of the entire 1 kb BglII insert of pULAD3 was determined using plasmid pULAD300 as the starting material. Since M13mp10 and M13mp11 have no KpnI site, the fragments with KpnI ends were first subcloned into pUC19 and then rescued as EcoRI-HindIII fragments and introduced into mp10 and mp11 digested with EcoRI and HindIII.

The complete nucleotide sequence of the active region shows an ORF1 of 339 nucleotides which encodes the putative SAF polypeptide (FIG. 6). There is only one possible open reading frame contained in the BglII-KpnI fragment starting with an ATG initiation codon at nt 183 and terminating with a TGA stop codon at nt 524 (ORF1 in FIGS. 5 and 6). Since the SstI-KpnI insert, contained in plasmid pULAD14, showed a lower degree of activity than plasmids containing also the upstream region of the SstI site (pULAD3, pULAD4, pULAD4 and pULAD6), it is very likely that the ATG (nt 219) also in frame with the presumptive saf reading frame may act as the initiation codon in pULAD10 and pULAD14. No other alternative initiation triplets are possible since a TGA termination codon exists upstream of the first ATG.

A long inverted repeat region, which may form a very stable stem and loop structure ($\Delta G = -53.6$ Kcal) is present upstream of the saf gene, from nt 90 to nt 135. Another hyphenated inverted repeat sequence was observed downstream from the terminator triplet of ORF1, extending from nucleotides 637 to 697, ($\Delta G = -38.4$ Kcal).

The saf gene has a high G+C content (76.3%) and a marked genes (Hopwood et al., Regulation of Gene Expression 25 Years On, Cambridge University Press, p.251–276, 1986).

Promoter Activity of the DNA Fragment Upstream of the ORF1

Since plasmids lacking the BglII-SstI fragment (from nt 1 to nt 216) were only expressed in one orientation (plasmids pULAD10 and pULAD14), but not in the opposite (plasmids pULAD9 and pULAD13), it seemed likely that the ORF1 promoter was located in that fragment. The presence of a transcription initiating sequence in this region was confirmed by subcloning this fragment into the promoter-probe plasmid pIJ486 (Ward et al., MOL. GEN. GENET. 203:468:478, 1986) which carried a: promoterless aminoglycoside phosphotransferase gene (neo). Expression of this gene confers kanamycin and neomycin resistance to *S.lividans.* The BglII-SstI fragment was subcloned into pIJ486 (the SstI end proximal to the neo gene) (plasmid named pIJ486::216). *S.lividans* transformed with pIJ486::216 was able to grow on MM containing more than 100 mcg/ml of km, whereas *S.lividans carrying pIJ*486 does not grow on MM with 5 mcg/ml of km. This result indicates that the BglII-SstI fragment has promoter activity. However, no typical "consensus" −10 or −35 regions were identified by nucleotide homology with other promoters of Streptomyces (Hopwood et al., Regulation of Gene Expression 25 Years On, Cambridge University Press, p.251–276. 1986).

Cloning of Amylase Gene

Figure 12:
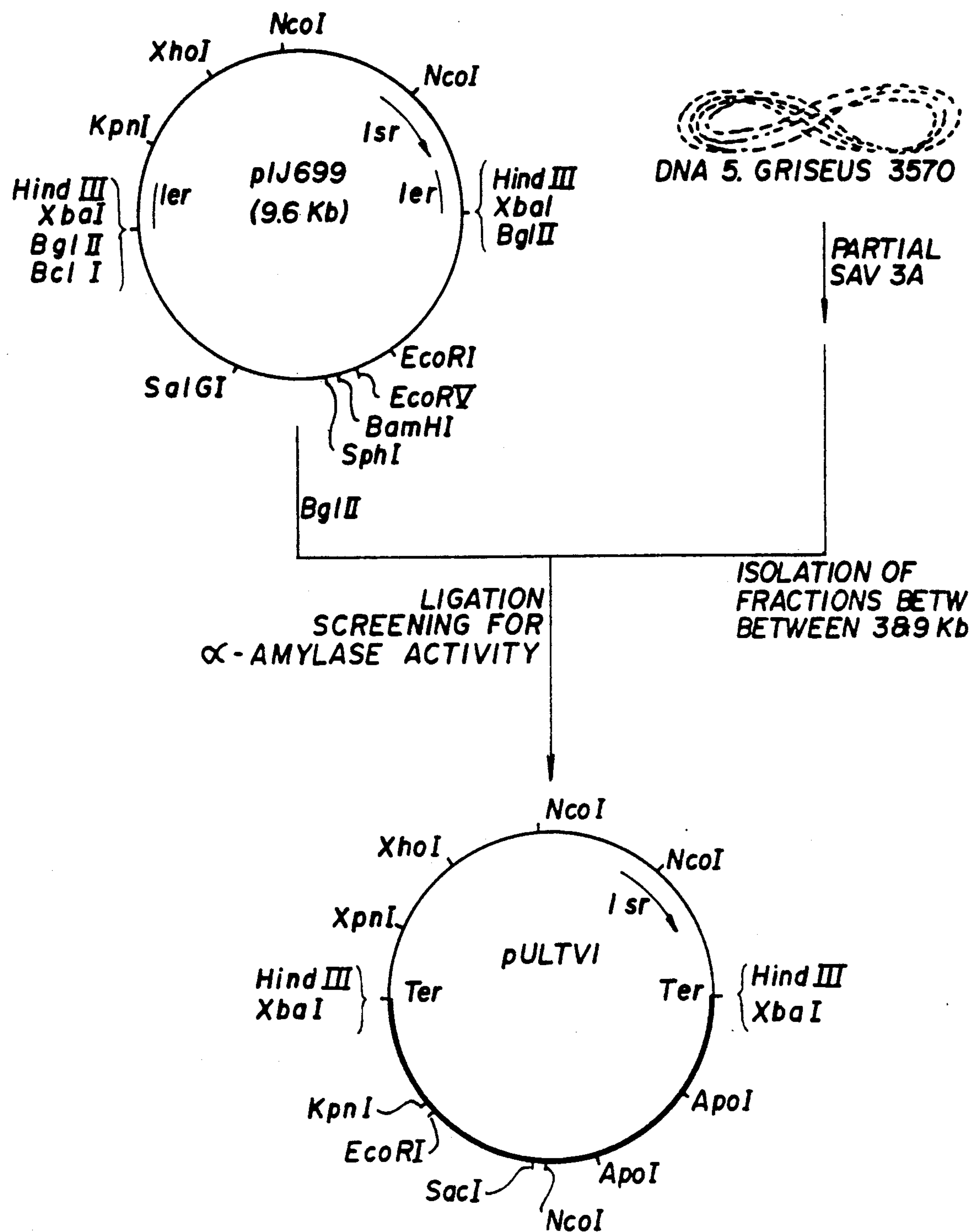
FIG. 12 The strategy used for cloning of the α-amylase gene of *S.griseus* IMRU 3570 using the plasmid pIJ699.

The definitive sequence of the amylase gene (amy) of *S.griseus* IMRU 3570 has now been elucidated. The complete sequence of nucleotides and inferred sequence of amino acids of the amylase gene of *S.griseus* appears in FIG. 11. The protein with the leader peptide has 566 amino acids (from nucleotide 318 to 2155, both inclusive), which corresponds to a PM of 59,713 D. Plasmid pULTV1 containing the entire α-amylase gene has been constructed by digesting the DNA of *S.griseus* IMRU 3570 with Sau3A, isolating the fractions of 3 to 9 Kb and ligating to BglII digested pIJ699. After screening for α-amylase activity the pULTV1 plasmid was selected which contained the entire α-amylase gene. The construction of pULTV1 is set forth in FIG. 12. Another way of obtaining a plasmid with the entire α-amylase gene is to construct it from two smaller fragments. Among the plasmids obtained by cloning the entire DNA library of *S.griseus* are those with a partial gene starting at the 5′ end and those with partial genes starting at the 3′ end. From the former a 1.3 Kb fragment BamHI-SacI, which includes the 5′ end of the gene can be obtained and from the latter a 1.2 Kb SacI-SalI fragment including the 3′ end of the gene can be extracted. Both can then be linked to pIJ2921 treated with SalI-BamHI, to obtain a plasmid with the intact native α-amylase gene (pULTV200).

Superior Potency of Saf Promoter

To test the expression of the amy gene under the control of different promoters, the production of amylase by *S.lividans* JI66 was studied. The amy gene was placed under the control of different promoters and amylase production was compared to that produced using the native promoter (Pamy). The promoters tested were that of the saf gene (Psaf), that of the $Km^r$ gene (Pneo), that of the synthetase PABA gene (Ppab) and that of the *E.coli* β-galactosidase gene (Plac). Plasmid pULTV220 containing the α-amylase gene without promoter was obtained by ligation of the EcoRI-BglII fragment, extracted from pULTV200, to the pUC18 digested with EcoRI-BamHI. The EcoRI-HindIII fragment from pULTV220 was ligated directly to the promoters of the saf, pab or $Km^r$ genes to obtain the pULVD10, pULVA1 and pULTV80 plasmids, respectively. pULTV150, containing the promoter of lac was obtained directly by HindIII digestion of pULTV220 and ligation to the 5 Kb HindIII fragment of the pIJ699.

The production studies of the resultant plasmids were carried out in dishes of MM +starch (1%)+thiostreptone, MM (1 mM P)+starch (1%)+thiostreptone, MM without phosphate+starch thiostreptone and MM+starch (1%)+thiostreptone+IPTG. pIJ699, pULTV100 and pULTV1 were used as controls. The relative measurement of amylase production was considered to be the area of circular corona obtained around each colony when staining the growth medium with $I_2$.

Figure 13:
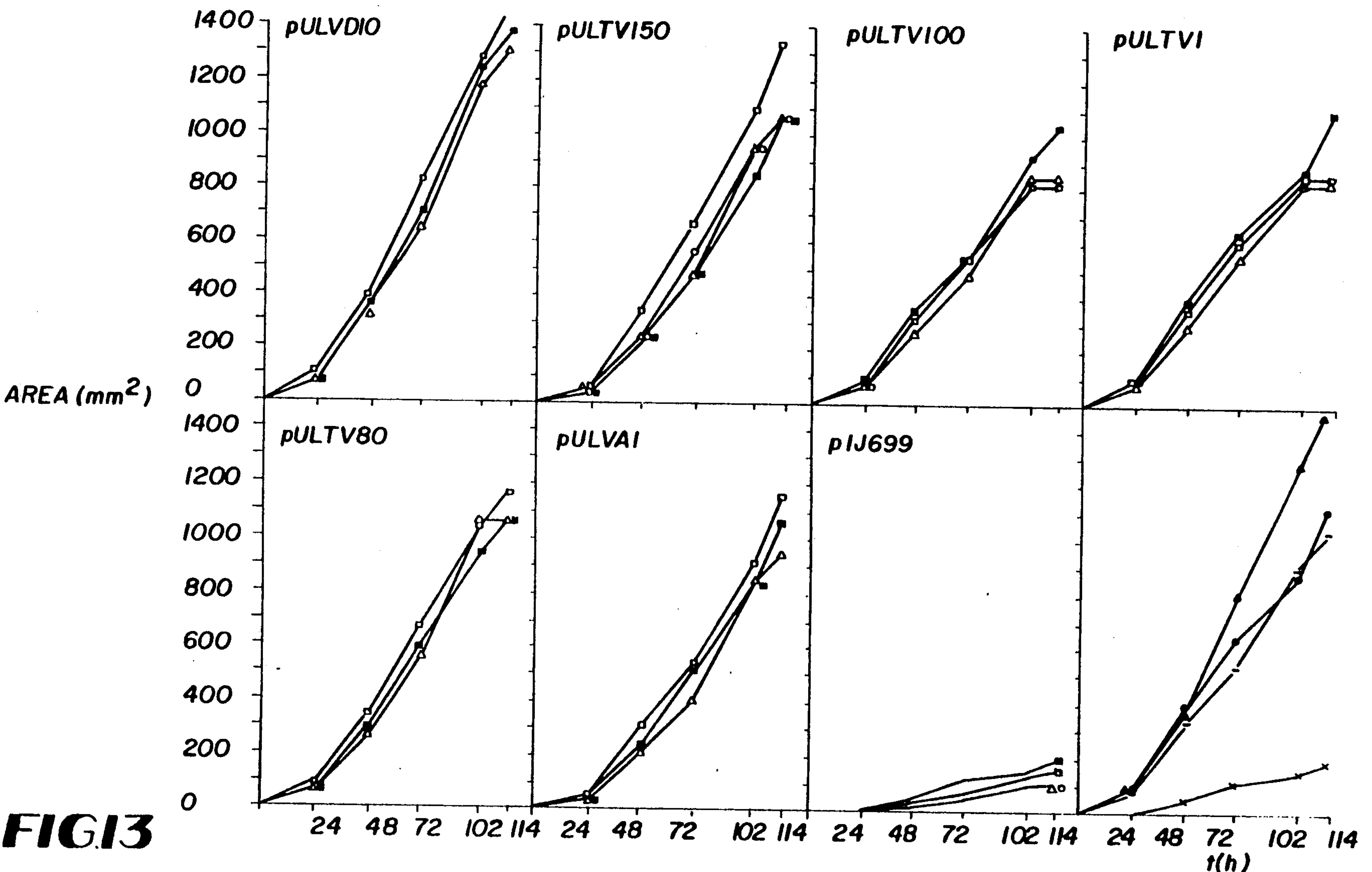
FIG. 13 A series of graphs show α-amylase production in dishes by different plasmids in the course of time and in different media.

The production graphs of the different constructions are set out in FIG. 13. Except in the controls, the highest production was achieved in MM (1 mM P) +starch +thiostreptone. It is clearly noticeable how the production peak was obtained with pULVD10 (which has the saf gene promoter) (1482 $mm^2$ as compared with the 1335 $mm^2$ of the second highest producer pULTV150, which bears the Plac promoter at 114 h of incubation).

In FIG. 13 (lower right-hand panel) the production values of pULVD10 are represented as compared with the controls in the best conditions so far known for each type of construction. The increase in pULVD10 production as compared with pULTV1 (native) is quite considerable: 1482 $mm^2$ as opposed to 1105 $mm^2$.

Thus, the saf gene promoter can be used as a substitute for other native promoters to improve expression of various endogenous Streptomyces polypeptides and proteins. Similarly, if a foreign DNA is inserted, the saf gene promoter will be expected to provide similar superior results as were demonstrated with amylase.

Expression of Foreign Polypeptide or Protein

To express a foreign polypeptide or protein the foreign DNA is preferably inserted at a suitable recognition site of an endogenous gene, preferably a gene encoding an extracellular enzyme so as to ensure secretion of the foreign polypeptide or protein. When the gene is the amylase gene, a suitable recognition site is the BstEII site (see FIG. 11). The foreign DNA is preferably inserted in such a way as to retain the secretion signals as much as possible from the extracellular enzyme gene. While these signals are predominantly on the leader sequence, there is evidence with respect to the amylase gene that the terminal carboxyl end is also important for secretion. Thus, it may be best to create a fusion protein by inserting the foreign DNA into the endogenous DNA, rather than removing the transcriptional part of the endogenous DNA and substituting the foreign DNA.

It is known that the saf gene controls the production of extracellular enzymes in the chromosomal DNA. Presumably, there are recognition sequences in the chromosomal DNA which recognize the SAF polypeptide and cause enhancement of extracellular enzyme production. The combination of the saf gene with the amylase gene on a plasmid does not cause increased production of amylase. Thus, it is preferred to place the foreign protein operatively linked to the secretion signal sequence of an endogenous extracellular enzyme which is controllable by SAF and, preferably, further operatively linked to the saf promoter (in the absence of the native promoter), into the chromosomal DNA as opposed to a plasmid. In this way, production of the foreign polypeptide or protein will be further enhanced by the native SAF. In a further preferred embodiment, the saf gene will be inserted by means of a plasmid into the same organisms in which the foreign DNA has been inserted into the chromosomal DNA. This will ensure enhanced secretion of the foreign polypeptide or protein.

DNA fragments may be cloned into the chromosomal DNA of Streptomyces by means of any of the known bacteriophage vectors for Streptomyces, such as $\phi$C31 or R4 (Chater et al, "Gene Cloning in Streptomyces" in *Gene Cloning in Organisms Other Than E.coli*, edited by P. H. Hofschneider et al, Springer-Verlag, Berlin, 1982, pages 87-95).

The diagram of FIG. 14 shows the preferred technique for obtaining secretion of a foreign protein, in this case CRF, from Streptomyces. KC 400 is a $\phi$31 derivative which lacks the attachment site (att$^-$) and has the $C^+$ gene. See Chater, K. F. et al "Mutational cloning in Streptomyces and the isolation of antibiotic production genes," Gene, 26:67-78 (1983). The $C^+$ gene encodes the repressor necessary for maintaining the lysogenic state. The att site in the wild type phage directs the attachment of the phage to the host cell DNA and directs the liberation therefrom. Without the att site, the phage cannot be integrated into the host chromosome unless a homologous DNA fragment is cloned into it. Any endogenous gene in the host strain may be used for this purpose and, thus, it is merely designated as "gene X" in FIG. 14. The phage $\phi$31 KC 400 is engineered by known techniques (see Hopwood, D. A. et al "Genetic manipulation of Streptomyces. A Laboratory Manual", The John Innes Foundation, Norwich, U.K. (1985)) to insert the homologous gene fragment (gene X) as well as a gene including the saf promoter and the endogenous $\alpha$-amylase gene with the gene for CRF operatively linked to and in reading frame with the $\alpha$-amylase gene. After infection of a host Streptomyces strain, preferably *S.coelicolor* A3(2) (available from the collection at the John Innes Institute, Norwich, U.K.), by this phage, the entire phage DNA will be inserted into the chromosomal DNA of the host cell, beginning at the homologous gene X, preferably using Campbell-type recombination. As indicated, all of the specific techniques for accomplishing this are within the skill of those of ordinary skill in this art so that such insertion can take place without undue experimentation.

The cells with the inserted chromosomal gene are then treated to take up the pULAD3 plasmid. Such cells will express the SAF polypeptide which in turn will enhance the secretion of "$\alpha$-amylase" by the chromosomal gene. The presence of the saf promoter on this gene will further enhance secretion of the "camylase." The "$\alpha$-amylase" secreted will include the CRF molecule fused thereto which can be readily separated by appropriate enzymatic digestion.

While $\alpha$-amylase gene of Streptomyces has been specifically exemplified, it should be understood that for the purpose of enhancing expression through use of the saf promoter, the gene for any polypeptide or protein produced by the Streptomyces species being used can be modified by removing the native promoter and substituting the saf promoter. Similarly, the foreign polypeptide or protein can be inserted into any such endogenous gene. Preferably, however, the endogenous gene selected will be one which expresses the protein through the cell wall and into the culture medium, in which case it is important to retain the secretion signal sequence. The best results will be obtained when the gene being selected for insertion of the foreign gene is one which is controlled by SAF and the insertion is in the chromosomal DNA, preferably with the concurrent insertion of a plasmid containing the saf gene.

While CRF has been specifically mentioned, it should be understood that the foreign DNA sequence may be any non-Streptomyces-derived DNA sequence encoding a protein or polypeptide, particularly one of eukaryotic or viral origin. Examples of such eukaryotic and viral DNA sequences are sequences encoding human and animal leukocyte interferons (IFN-α), fibroblast interferons (IFN-β), and immune interferons (IFN-γ), human insulin, human and animal growth and other hormones, such as corticotropin releasing factor (CRF), human serum albumin and various human blood factors and plasminogen activators, both tissue and urokinase, hepatitis B viral core and surface antigens, FMD viral antigens and other human, animal and viral polypeptides and proteins.

While the saf promoter is preferred, production of the foreign polypeptide or protein will further be enhanced by transforming the host cell with an expression vector containing the saf gene. This expression vector may be in the plasmid DNA of the cell. Thus, the endogenous promoter or any other promoter may be used and still obtain secretion of the foreign polypeptide or protein.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

TABLE I

| Bacterial Strains | | |
|---|---|---|
| Designation | Relevant characteristics | Source of reference |
| *S. griseus* ATCC 10137 | wild type | ATCC |
| *S. griseus* JI 2212 | wild type | JI |
| *S. griseus* IMRU 3570 | wild type | IMRU |
| *S. lividans* JI 1326 | wild type | JI |
| *S. acrimycini* JI 2236 | wild type | JI |
| *S. coelicolor* JI 2280 | CysE24, PabA1, strl | JI |
| *S. coelicolor* JI 1157 | wild type | JI |
| *S. clavuligerus* NRRL 3585 | wild type | NRRL |
| *S. lactamdurans* NRRL 3802 | wild type | NRRL |
| *S. albus* G | wild type | JI |
| *E. coli* E15 | phoA8 | CGSC |
| *E. coli* AW1046 | PhoA, phoC, tsX::tn5, leu, Kan ® | 1 |
| *E. coli* H2 (*E. coli* CGSC 5259) | phoB52, pho-35 | CGSC |
| *E. coli* JM103 | proAB, lacZ M15 | 2 |

JI: Collection of microorganisms of the John Innes Institute. Coleny Lane, Norwich NR4 UH, United Kingdom.
ATCC: American Type Culture Collection.
IMRU: Waksmans Institute of Microbiology, Rutgers University, New Brunswick, N.J., USA.
NRRL: Northern Regional Research Laboratories, Peoria, ILL. USA.
CGSC: *E. coli* Genetic Stock Center

TABLE 2

| Plasmids and Phages | | |
|---|---|---|
| Designation | Relevant characteristics | Source of reference |
| pIJ702 | Thiostrepton resistance and melanine+ | 3 |
| pIJ699 | Thiostrepton, viomycin and Kanamycin resistances | 4 |
| pIJ61 | Thiostrepton and neomycin resistances | 5 |
| pIJ486 | Thiostrepton resistance and saf gene without promoter | 6 |
| pULAD series | Streptomyces and *E. coli* vectors carrying saf gene and/or adjacent sequences | This work |
| pIJ486::216 | pIJ486 carrying the saf promoter region | This work |
| pUC19 | bla+, lacZpZoZ' | 7 |
| pIJ2921 | bla+, lacZpZoZ' | See FIG. 10 |
| M13 mp10 and mp11 | Phages for generation of single-stranded DNA | 8 |
| pULTV1 and 200 | Streptomyces vectors carrying amylase gene | This work |
| pULTV220 | Streptomyces vector carrying promoterless amylase gene | This work |
| pULVD10 | Streptomyces vector carrying amylase gene with saf promoter | This work |
| pULVA1 | Streptomyces vector carrying amylase gene with pab promoter | This work |
| pULTV80 | Streptomyces vector carrying amylase gene with Km$^r$. promoter | This work |
| pULTV150 | Streptomyces vector carrying amylase gene with lac promoter | This work |

References Quoted in Tables 1 and 2

1. Hoffman, C. S., and A. Wright. 1985. Fusions of secreted proteins to alkaline phosphatase: an approach for studying protein secretion. Proc. Natl. Acad. Sci. USA 82:5107-5111.
2. Messing, J., R. Crea, and P. H. Seeburg. 1981. A system for shotgun DNA sequencing. Nucl. Acids. Res. 9:309-321.
3. Katz, E., C. J. Thompson, and D. A. Hopwood. 1983. Cloning and expression of the tyrosinase gene from *Streptomyces antibioticus* in *Streptomyces lividans*. J. Gen. Microbiol. 129:2703-2714.
4. Kieser, T., and R. E. Melton. 1988. Plasmid pIJ699, a multicopy positive-selection vector for Streptomyces. Gene 65:83-91.
5. Hopwood, D. A., M. J., Bibb, K. F. Chater, T. Kieser, C. J. Bruton, H. M. Kieser, D. J. Lydiate, C. P., Smith, J. M. Ward, and H. Schrempf. 1985. Genetic manipulation of Streptomyces. A Laboratory Manual. The John Innes Foundation, Norwich, U.K.
6. Ward, J. M., G. R. Janssen, T. Kieser, M. J. Bibb, M. J. Buttner, and M. J. Bibb. 1986. Construction and characterization of a series of multi-copy promoter-probe plasmid vectors for Streptomyces using the aminoglycoside phosphotransferase gene from Tn5 as indicator. Mol. Gen. Genet. 203:468-478.
7. Yanisch-Perron, C., J. Vieira, and J. Messing. 1985. Improved M13 phage cloning vectors and host strains: nucleotide sequences of the M13mp18 and pUC19 vectors. GENE 33:103-119.
8. Messing, J. 1983. New M13 Vectors for Cloning. Methods Enzymol. 101:20-78.

What we claim is:

1. DNA consisting essentially of a DNA sequence coding for a polypeptide having the following amino acid sequence:

Met Cys Ser Ala Val Val Ala Ala Ala Val Ser Ser Met Ser Arg

Arg Arg Arg Arg Ala Ser Ala Thr Arg Arg Ser Ala Ala Val Ser

Pro Pro His Thr Pro Tyr Gly Ser Gly Cys Ile Ser Ala Cys Ser

Trp His Ser Thr Ile Thr Gly His Arg Ala Gln Thr Arg Leu Ala

Ala Ser Ser Arg Ala Ser Arg Ala Ala Val Gly Ser Phe Asp Gly

Ala Lys Asn Arg Pro Ala Ser Ser Arg Arg Gln Ala Ala Ser Glu

Cys Gln Gly Pro Ala Ser Ser Ser Arg Ala Gly Val Arg Trp Ala

-continued

Gly Thr Ala Ala Asn Gly Arg Gly ter.

2. DNA in accordance with claim 1 comprising the following nucleotide sequence:

ATG TGC TCG GCC GTC GTC GCG GCG GCC
GTG AGC TCG ATG TCC CGC
CGT CGC CGC CGG GCC AGC GCC ACC CGG
CGC TCC GCT GCG GTG AGC
CCG CCC CAC ACT CCG TAC CGC TCG GGC
TGT ACT AGC GCG TGC TCC
TGG CAC TCC ACC ATC ACC GGA CAC CGG
GCA CAG ACC CGC TTG GCC
GCC TCC TCG CGG GCC AGC CGG GCG GCG
GTC GGC TCC TTC GAC GGG
GCG AAG AAC AGG CCG GCC TCG TCG CGG
CGG CAG GCC GCA TCG GAA
TGC CAG GGG CCC GCG TCG TCC TCC CGT
GCG GGG GTC CGC TGG GCC
GGA ACG GCG GCG AAC GGC AGA GGC TGA.

3. DNA consisting essentially of a DNA sequence which hybridizes under stringent conditions with the following nucleotide sequence:

ATG TGC TCG GCC GTC GTC GCG GCG GCC GTG AGC TCG ATG TCC CGC
CGT CGC CGC CGG GCC AGC GCC ACC CGG CGC TCC GCT GCG GTG AGC
CCG CCC CAC ACT CCG TAC CGC TCG GGC TGT ACT AGC GCG TGC TCC
TGG CAC TCC ACC ATC ACC GGA CAC CGG GCA CAG ACC CGC TTG GCC
GCC TCC TCG CGG GCC AGC CGG GCG GCG GTC GGC TCC TTC GAC GGG
GCG AAG AAC AGG CCG GCC TCG TCG CGG CGG CAG GCC GCA TCG GAA
TGC CAG GGG CCC GCG TCG TCC TCC CGT GCG GGG GTC CGC TGG GCC
GGA ACG GCG GCG AAC GGC AGA GGC TGA and which codes for a polypeptide having substantially the same activity in increasing production of extracellular enzymes as that of the polypeptide coded for by the nucleotide sequence set forth in this claim.

4. A vector containing a DNA sequence according to claim 1.

5. A vector according to claim 4 wherein the DNA sequence includes a regulator unit for promoting expression of the polypeptide encoded by said DNA.

6. A vector according to claim 5, wherein the regulatory unit upstream to the ATG has the following nucleotide sequence:

AGATCTCCTCGTCCCACCGGCTGTCGAAGCTCCGCGCCTACAGCGCCATCGACTTCGACCGGG
CGAAATAGGAAGCGGCCGGCGACAAAACGGGGAGGGGCGGGAAACGGTGGTCCGTTTCCCGCC
CCTGCCCGTAGGCCGTGCGCGTCCCGCCGGTGCGCGGCGTTCAGCCCGCCGCCGCT.

7. A Streptomyces host cell transformed with a vector according to claim 4.

8. A process for preparing a polypeptide by culturing a host cell according to claim 7 and recovering the polypeptide produced thereby.

9. A vector containing a DNA sequence according to claim 2.

10. A vector according to claim 9, wherein the DNA sequence includes a regulatory unit for promoting expression of the polypeptide encoded by said DNA.

11. A vector according to claim 10, wherein the regulatory unit upstream to the ATG has the following nucleotide sequence:

AGATCTCCTCGTCCCACCGGCTGTCGAAGCTCCGCGCCTACAGCGCCATCGACTTCGACCGGG
CGAAATAGGAAGCGGCCGGCGACAAAACGGGGAGGGGCGGGAAACGGTGGTCCGTTTCCCGCC
CCTGCCCGTAGGCCGTGCGCGTCCCGCCGGTGCGCGGCGTTCAGCCCGCCGCCGCT.

12. A Streptomyces host cell transformed with a vector according to claim 9.

13. A process for preparing a polypeptide by culturing a host cell according to claim 12 and recovering the polypeptide produced thereby.

14. A vector containing a DNA sequence according to claim 3.

15. A vector according to claim 14, wherein the DNA sequence includes a regulatory unit for promoting expression of the polypeptide encoded by said DNA.

16. A vector according to claim 15, wherein the regulatory unit upstream to the ATG has the following nucleotide sequence:

AGATCTCCTCGTCCCACCGGCTGTCGAAGCTCCGCGCCTACAGCGCCATCGACTTCGACCGGG
CGAAATAGGAAGCGGCCGGCGACAAAACGGGGAGGGGCGGGAAACGGTGGTCCGTTTCCCGCC
CCTGCCCGTAGGCCGTGCGCGTCCCGCCGGTGCGCGGCGTTCAGCCCGCCGCCGCT.

17. A Streptomyces host cell transformed with a vector according to claim 14.

18. A process for preparing a polypeptide by culturing a host cell according to claim 17 and recovering the polypeptide produced thereby.

19. Plasmid pULAD3.

20. A promoter having the following DNA sequence:

AGATCTCCTCGTCCCACCGGCTGTCGAAGCTCCGCGCCTACAGCGCCATCGACTTCGACCGGG
CGAAGTAGGAAGCGGCCGGCGACAAAACGGGGAGGGGCGGGAAACGGTGGTCCGTTTCCCGCC

-continued

CCTGCCCGTAGGCCGTGCGCGTCCCGCCGGTGCGCGGCGTTCAGCCCGCCGCCGCT.

21. A cloning vehicle comprising a DNA sequence encoding a polypeptide or protein operatively linked to a promoter in accordance with claim 20.

22. A cloning vehicle in accordance with claim 21 wherein said DNA sequence is one which is endogenous to Streptomyces.

23. A cloning vehicle in accordance with claim 21, wherein said DNA sequence comprises all or part of a sequence encoding a polypeptide or protein endogenous to Streptomyces to which has been fused, in the same reading frame, a DNA sequence encoding a non-Streptomyces polypeptide or protein.

24. A Streptomyces host cell transformed with a cloning vehicle in accordance with claim 21.

25. A Streptomyces host cell transformed with a cloning vehicle in accordance with claim 22.

26. A Streptomyces host cell transformed with a cloning vehicle in accordance with claim 23.

27. A method of expressing a foreign DNA sequence in Streptomyces comprising operatively linking said foreign DNA sequence to a Streptomyces expression control sequence including the promoter in accordance with claim 20.

28. A method in accordance with claim 27, wherein the foreign DNA sequence and Streptomyces expression control sequence are inserted in the chromosomal DNA of the Streptomyces.

29. A method in accordance with claim 28, wherein the host Streptomyces further includes a plasmid capable of expressing a polypeptide of the SAF type.

30. A method in accordance with claim 27, wherein said foreign DNA sequence is operatively linked to said Streptomyces expression control sequence through a DNA sequence encoding at least a part of the signal sequence of a protein or polypeptide secreted from Streptomyces, said DNA sequence encoding the signal sequence being expressed together with said foreign DNA sequence under the control of said Streptomyces expression control sequence to afford secretion of the protein or polypeptide coded for by the foreign DNA sequence.

* * * * *